United States Patent
Mallinger et al.

(10) Patent No.: US 7,314,454 B2
(45) Date of Patent: Jan. 1, 2008

(54) METHOD OF PREVENTING EYE-RELATED POSITIONAL INJURIES DURING SPINAL SURGERY

(76) Inventors: Joseph C. Mallinger, 28417 Tricia Pl., Escondido, CA (US) 92026; Ray Linovitz, P.O. Box 1671, Rancho Santa Fe, CA (US) 92067; Arthur C. Perry, P.O. Box 1102, Rancho Santa Fe, CA (US) 92067

( * ) Notice: Subject to any disclaimer, the term of this patent is extended or adjusted under 35 U.S.C. 154(b) by 352 days.

(21) Appl. No.: 11/146,570

(22) Filed: Jun. 7, 2005

(65) Prior Publication Data

US 2006/0276725 A1 Dec. 7, 2006

(51) Int. Cl.
*A61B 5/103* (2006.01)
*A61B 5/117* (2006.01)
(52) U.S. Cl. .................. 600/587; 600/398; 600/553; 128/898
(58) Field of Classification Search ............... 600/383, 600/398, 587, 553; 128/897, 898
See application file for complete search history.

(56) References Cited

U.S. PATENT DOCUMENTS

| | | |
|---|---|---|
| 3,757,770 A | 9/1973 | Brayshaw et al. |
| 4,089,329 A | 5/1978 | Couvillon |
| 4,165,736 A | 8/1979 | Wolfson |
| 4,281,662 A | 8/1981 | Brent |
| 4,548,205 A | 10/1985 | Armeniades et al. |
| 4,825,873 A | 5/1989 | Kohayakawa |
| 4,836,219 A | 6/1989 | Hobson et al. |
| 4,863,259 A | 9/1989 | Schneider et al. |
| 4,922,913 A | 5/1990 | Waters, Jr. et al. |
| 4,969,472 A | 11/1990 | Langley et al. |
| 4,981,139 A | 1/1991 | Pfohl |
| 5,032,020 A | 7/1991 | Robert |
| 5,092,334 A | 3/1992 | Nishio et al. |
| 5,179,953 A | 1/1993 | Kursar |
| 5,183,044 A | 2/1993 | Nishio et al. |
| 5,215,523 A | 6/1993 | Williams et al. |
| 5,217,015 A | 6/1993 | Kaye et al. |

(Continued)

FOREIGN PATENT DOCUMENTS

JP  01212565 A  8/1989

(Continued)

OTHER PUBLICATIONS

White, Emert. "Care of the eye during anaesthesia." 2004. Anaesthesia and Intensive Care Medicine. vol. 5 No. 9. pp. 302-303.*

*Primary Examiner*—Max F. Hindenburg
*Assistant Examiner*—John Pani
(74) *Attorney, Agent, or Firm*—Stephen C. Beuerle; Procopio Cory Hargreaves & Savitch LLP

(57) ABSTRACT

A method of preventing eye-related positional injuries during spinal surgery includes providing an orbital area pressure monitoring system including a site sensor with transducer, and a monitor connected to the site sensor; using the orbital area pressure monitoring system to continuously monitor pressure on an orbital area of the patient with the site sensor and monitor; and causing an alarm to be actuated to alert medical personnel of a pressure condition when monitored pressure is greater than a predetermined threshold.

14 Claims, 3 Drawing Sheets

U.S. PATENT DOCUMENTS

| | | |
|---|---|---|
| 5,284,154 A | 2/1994 | Raymond et al. |
| 5,349,955 A | 9/1994 | Suzuki |
| 5,396,888 A | 3/1995 | Massie et al. |
| 5,415,167 A | 5/1995 | Wilk |
| 5,523,808 A | 6/1996 | Kohayakawa |
| 5,579,765 A | 12/1996 | Cox et al. |
| 5,613,501 A * | 3/1997 | Michelson ............ 5/637 |
| 5,634,468 A | 6/1997 | Platt et al. |
| 5,813,982 A | 9/1998 | Baratta |
| 5,887,590 A | 3/1999 | Price |
| 5,914,660 A | 6/1999 | Mesibov et al. |
| 5,916,179 A | 6/1999 | Sharrock |
| 6,193,659 B1 | 2/2001 | Ramamurthy et al. |
| 6,238,338 B1 | 5/2001 | DeLuca et al. |
| 6,447,449 B1 | 9/2002 | Fleischman et al. |
| 6,572,636 B1 | 6/2003 | Hagen et al. |
| 6,579,235 B1 | 6/2003 | Abita et al. |
| 6,749,568 B2 | 6/2004 | Fleischman et al. |
| 6,814,706 B2 | 11/2004 | Barton et al. |
| 2002/0100481 A1 | 8/2002 | Abbasi |
| 2003/0149349 A1 | 8/2003 | Jensen |
| 2004/0074502 A1 | 4/2004 | Abbasi |
| 2004/0215098 A1 | 10/2004 | Barton et al. |
| 2004/0242976 A1 | 12/2004 | Abreu |

FOREIGN PATENT DOCUMENTS

| | | |
|---|---|---|
| WO | WO 2004/078038 | 9/2004 |

* cited by examiner

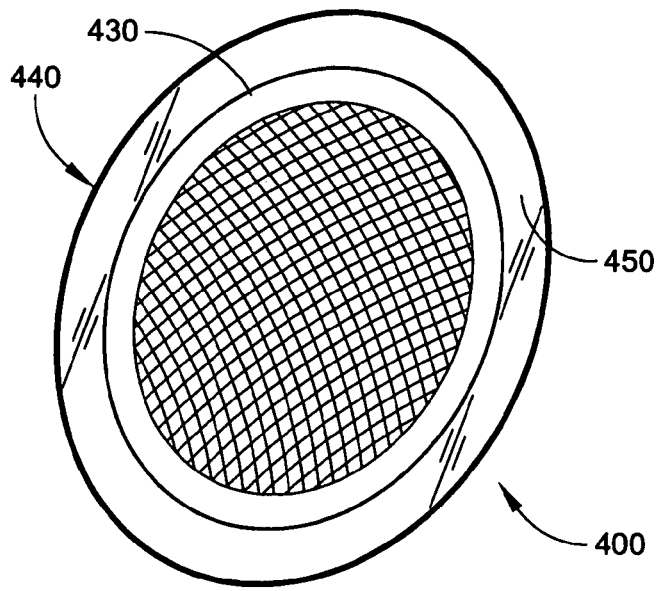
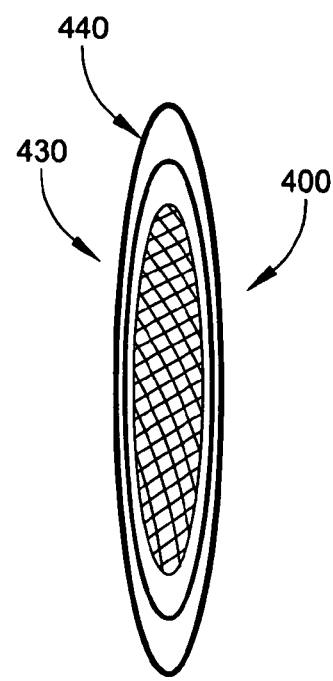
FIG. 5  FIG. 6
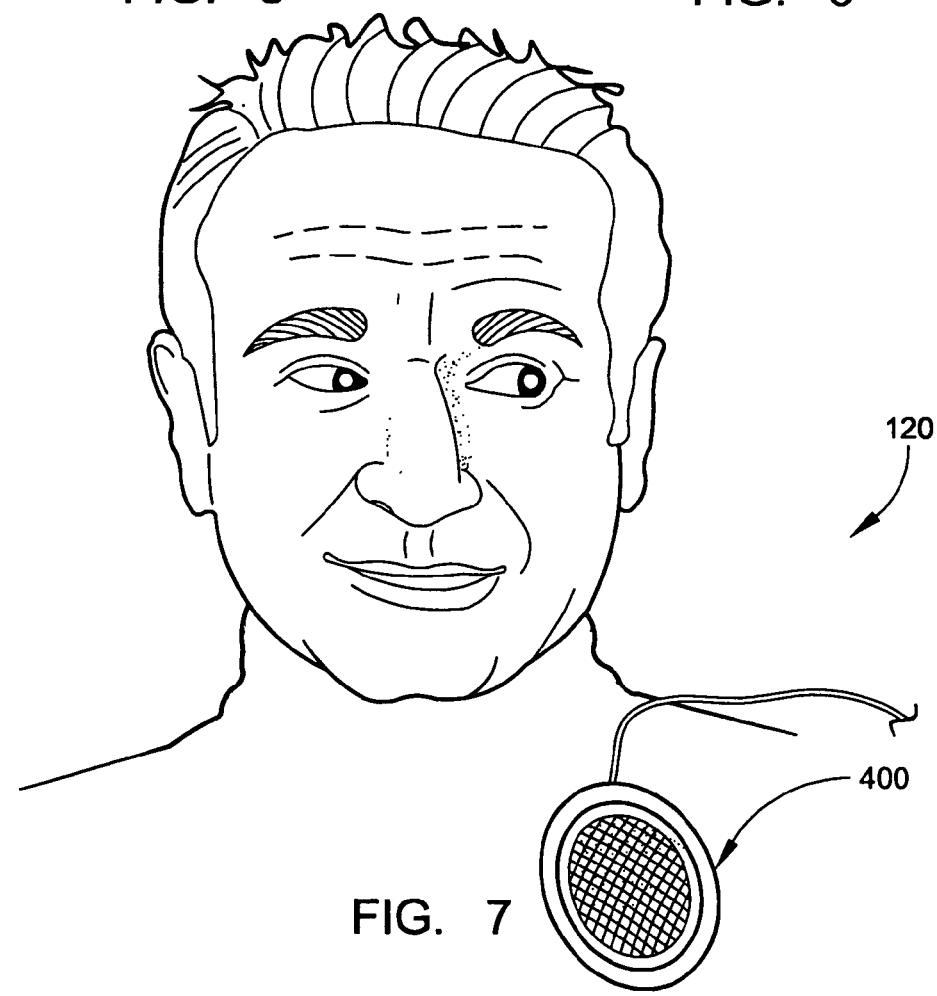
FIG. 7

METHOD OF PREVENTING EYE-RELATED POSITIONAL INJURIES DURING SPINAL SURGERY

FIELD OF THE INVENTION

The present invention relates to systems and methods for preventing eye-related positional injuries during spinal surgery.

BACKGROUND OF THE INVENTION

During spinal surgery, a patient lays asleep on an operating table in a prone position so that the patient's back is easily accessed. The patient's face is directed downward, towards the floor, and is supported by a sponge-like support. The sponge-like support has a cut-out for the patient's eyes, nose, and mouth. If the patient's head moves or rolls relative to the sponge-like support during the procedure, this can cause external pressure on the orbital area (i.e. the eye, the orbital socket, and the area around the eye). Direct or indirect pressure may be put on the eyeball or on the nerves in the orbital area, especially in the super orbital region. The patient is unaware of this because the patient is asleep during the lengthy procedure (e.g., eight hours, ten hours, twelve hours). The direct pressure can cause blood flow to stop in the orbital area. The direct pressure on the orbital area and/or the diminished blood flow to the eye caused by this external pressure is believed by the present inventors to be a possible cause of intraocular, periorbital, or periocular injuries to the eye(s) of the patient during spinal surgery. These injuries can result in blindness or other injuries.

SUMMARY OF THE INVENTION

The present invention involves a method of using a pair of adhesive transducer patches over the orbital areas of a patient during spinal surgery to detect and prevent pressure on or around the eyes during such a procedure. The patches are placed over the orbital areas prior to the spinal surgery and are worn by the patient during surgery. Each patch includes a transducer that detects pressure. A monitor is coupled to the patches, and actuates an alarm in the event of an "eye pressure condition".

Another aspect of the invention involves a method of preventing eye-related positional injuries during spinal surgery. The method includes putting a spinal surgery patient under general anesthesia; adding an ointment to an eye of the patient; maintaining the patient's eye in a closed condition during the spinal surgery; providing a site sensor to detect pressure on an orbital areas of the patient, the site sensor including a transducer; adhering the site sensor to the patient over the orbital areas of the patient; providing a facial support to support the patient's face during the spinal surgery, the facial support including an opening to accommodate the site sensor on the orbital areas of the patient; providing the patient in a prone position with the patient's face supported by the facial support with the site sensor accommodated by the opening; connecting the site sensor to a monitor to monitor pressure on the orbital areas of the patient with the site sensor; continuously monitoring pressure on the orbital areas of the patient with the site sensor and monitor; alerting medical personnel of a pressure condition on the orbital areas if the monitor and site sensor determines a pressure condition exists on the orbital areas; and readjusting the patient's head to alleviate the pressure condition, preventing eye-related positional injuries.

A further aspect of the invention involves a method of preventing eye-related positional injuries during spinal surgery. The method includes attaching a sensor to a spinal surgery patient over an orbital area of the patient, the site sensor including a transducer; connecting the site sensor to a monitor; continuously monitoring pressure on the orbital areas of the patient with the site sensor and monitor; alerting medical personnel of a pressure condition on the orbital areas if the monitor and site sensor determine a pressure condition exists on the orbital areas; and readjusting the patient's head to alleviate the pressure condition, preventing eye-related positional injuries.

A still further aspect of the invention involves a method of preventing eye-related positional injuries during spinal surgery. The method includes providing an orbital area pressure monitoring system including a site sensor with transducer, and a monitor connected to the site sensor; using the orbital area pressure monitoring system to continuously monitor pressure on an orbital area of the patient with the site sensor and monitor; and causing an alarm to be actuated to alert medical personnel of a pressure condition when monitored pressure is greater than a predetermined threshold.

Further objects and advantages will be apparent to those skilled in the art after a review of the drawings and the detailed description of the preferred embodiments set forth below.

BRIEF DESCRIPTION OF THE DRAWINGS

FIG. 5 is a rear elevational view of another embodiment of a site sensor.

FIG. 6 is rear perspective view of the site sensor shown in FIG. 5.

FIG. 7 shows the site sensor of FIGS. 5 and 6 applied to a patient's body in a location other than the orbital areas to show that the site sensor may be used to monitor excessive external pressure incurred by a patient placed in any position during any surgical procedure.

DETAILED DESCRIPTION OF PREFERRED EMBODIMENTS

Figure 1:
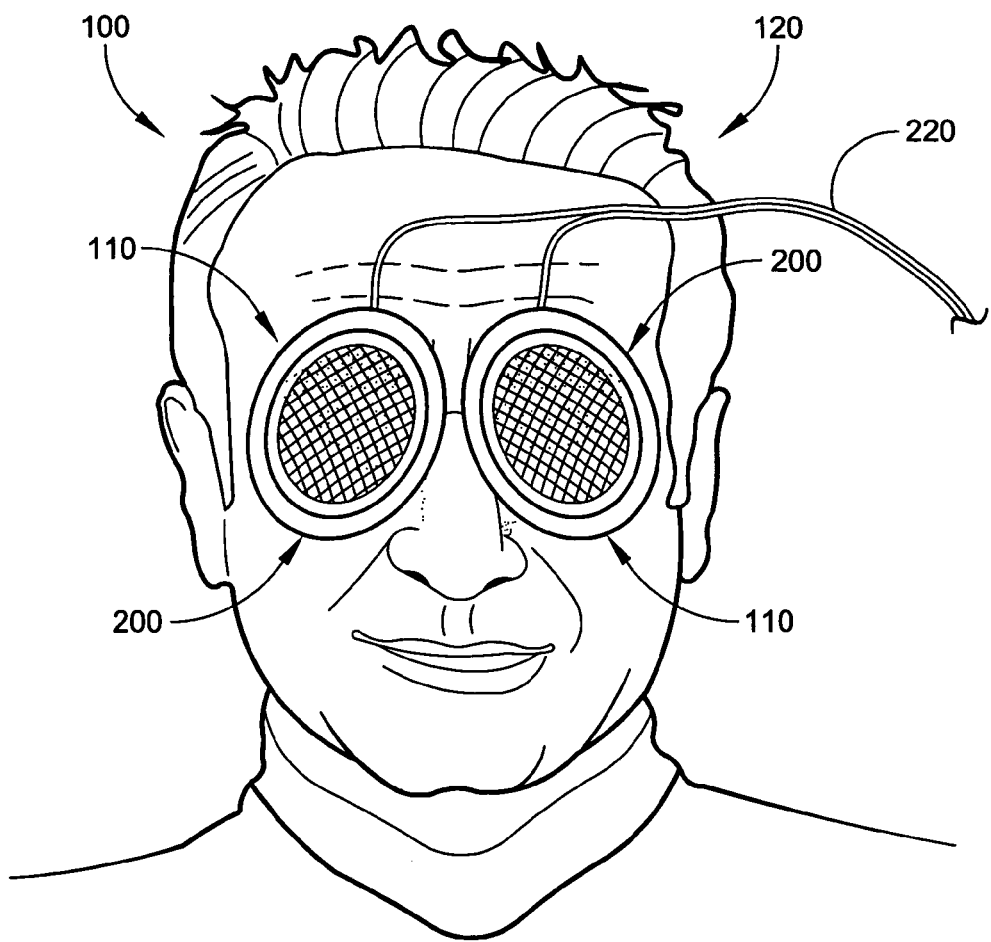
FIG. 1 is a front view of the patient's head during spinal surgery, and shows an embodiment of a pair of site sensors shown applied over the orbital areas of the patient.
Figure 2:
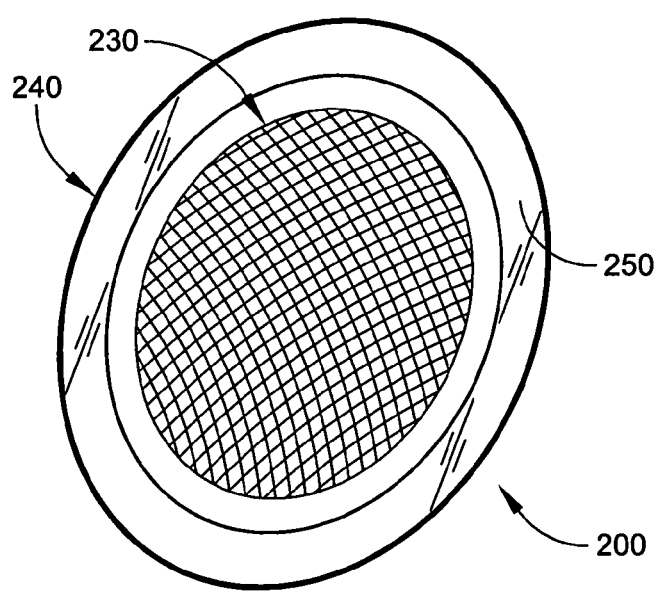
FIG. 2 is a rear elevational view of one of the site sensors shown in FIG. 1.
Figure 3:
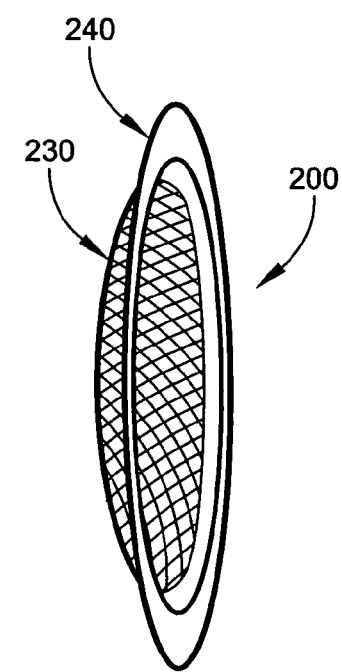
FIG. 3 is rear perspective view of the site sensor shown in FIG. 1.
Figure 4:
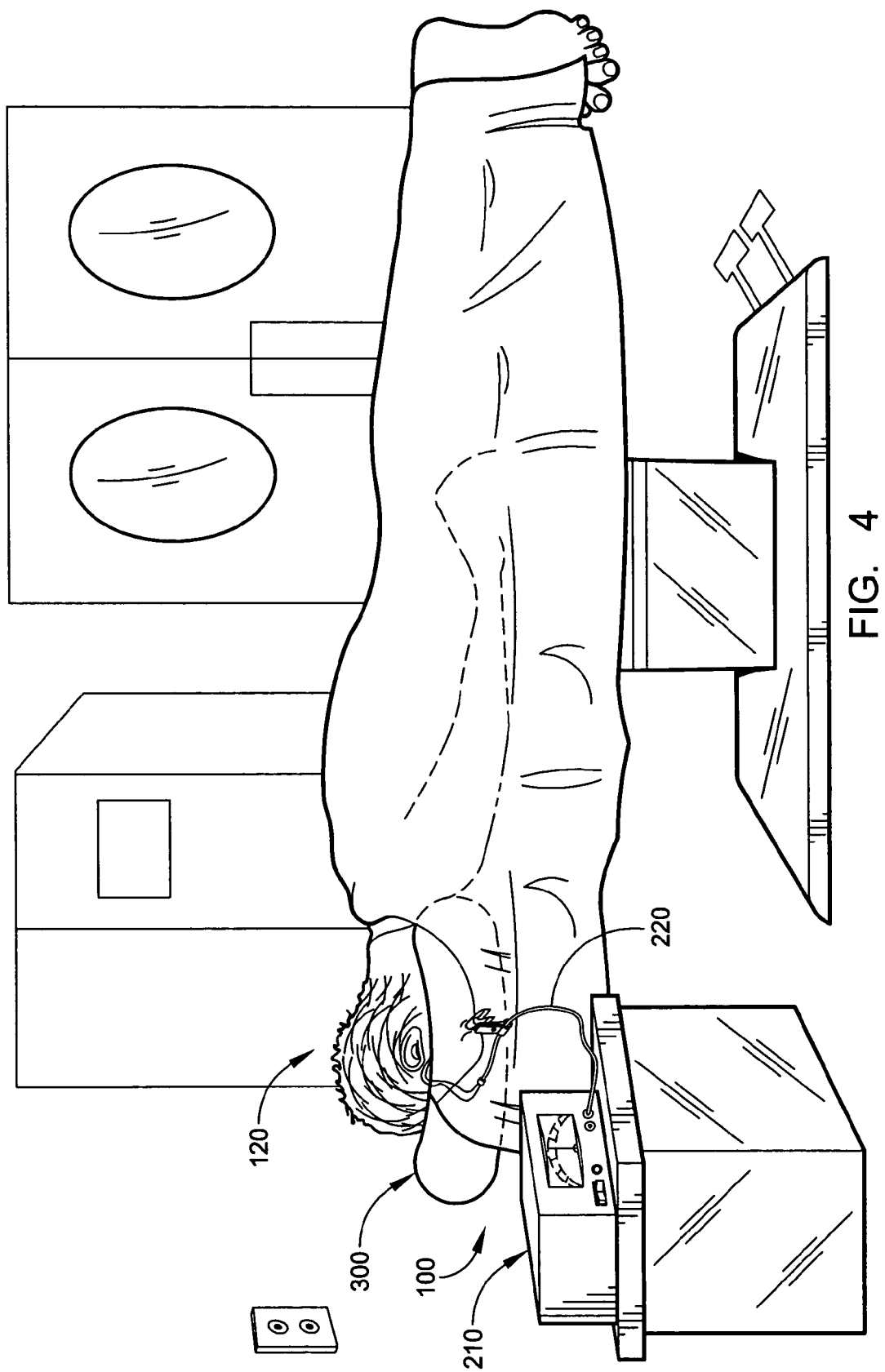
FIG. 4 is a side-elevational view of a patient lying prone on an operating table during a spinal procedure, and shows an embodiment of a monitor that may be coupled to the site sensors of the present invention through one or more wires.

With reference to FIGS. 1-4, an embodiment of a system 100 and method for monitoring external pressure on the orbital areas 110 of a patient 120 during prone position spinal surgery to prevent eye-related positional injuries such as, but not by way of limitation, posterior ischemic optic neuropathy (PION), anterior ischemic optic neuropathy (AION), cornea injuries, eyelid injuries, supraorbital nerve injuries, angle closure glaucoma, retina detachment, intraocular lens dislocation, infraorbital nerve injury, glaucoma bleb closure, iris ischemia, ciliary body ischemia, and other periorbital injuries, will be described. Although the system 100 and method will be discussed in conjunction with monitoring external pressure on the orbital areas 110 of a patient 120 during a spinal surgical procedure, the system 100 and method may be used in conjunction with monitoring external pressure on the orbital areas 110 of a patient 120 during other types of surgery, other than spinal surgery, where the patient is placed prone during the surgery. Further, the system 100 and method may be used for monitoring excessive external pressure or other conditions to prevent all positional injuries during a surgical procedure involving an anesthetized patient whether in the prone, supine, side-lying, jack-knifed, or other position. Some of these other positional injuries include, but not by way of limitation, cubital tunnel, carpal tunnel, peroneal palsy, and compartment syndromes.

The monitoring system 100 includes site sensors 200 connected to a monitor 210 (FIG. 4) via one or more wires 220. In the embodiment shown, each site sensor 200 is a substantially circular transducer patch and is made up of one or more appropriate medical-grade, biocompatible materials. The site sensor 200 includes a cupped transducer element 230 and a substantially annular ring 240 extending circumferentially outward from the periphery of the transducer element 230. An underside 250 of the ring 240 may be completely or partially coated or circumscribed with a coating of medical-grade, biocompatible adhesive, which is covered by a removable backing, to allow for the attachment of the site sensor 200 to the orbital area 110 on the patient 120. One or more lead wires 220 extending from the transducer element 230 may be connected to the monitor 210 for monitoring the condition of the site sensor 200. The one or more wires 220 may be disposed within a sheath or other covering.

A method of monitoring external pressure on the orbital areas 110 of a patient 120 during prone position spinal surgery to prevent eye-related positional injuries will be described. During a spinal procedure on the patient 120, the patient 120 is put asleep lying on his or her back using general anesthesia. In order to provide ventilation to the anesthetized patient's lungs, a tube (not shown) is placed into the patient's windpipe through the patient's mouth or nose, and then secured with tape. An ointment is added to the surface of the globe (eyeball) and the eyelids are taped closed so that the eyes do not open during the procedure to prevent corneal drying. The backing is removed from the adhesive underside 250 of the site sensors 200, and the site sensors 200 are affixed to the patient's skin, over the orbital areas 110. A facial cushion support 300 is put on the patient's face so that the orbital areas 110, site sensors 200, nose, and mouth are located within a cut-out of the facial cushion support 300. Then, the patient 102 is put over in a prone position, face-down on an operating table, similar to that shown in FIG. 4. The patient 100 is rolled over with pads on his or her chest, the patient's neck position is adjusted, and the anesthesiologist looks under the table and makes sure nothing has moved. The perimeter of the patient's face 110, especially the forehead and jaw, rests on the facial cushion support 300. The one or more wires 220 are connected to the monitor 210, and the monitor is activated. A visual check is made to ensure there is no pressure on the site sensors 200. At this point the pressure on the site sensors 200 should be zero. Pressure on the site sensors 200 is continuously monitored during the surgery. Additional parameters, conditions, or variables may be monitored during the surgical procedure.

During the spinal surgery, if the patient's head moves or rolls relative to the facial cushion support 300 and any pressure is applied to the orbital area 110, the barrier formed by the transducer element 230 is breached or deformed from its original shape. A electrical signal is sent from the monitor 210 to the site sensor 200, where the signal passes through the transducer element 230, and back out to the monitor 210. The monitor 210 monitors the return signal. The breach or deformation of the barrier of the transducer element 230 causes the returned signal to the monitor 210 to be outside of a designated range or above/below a predetermined threshold. An alarm output is produced and the monitor 250 actuates an alarm. The alarm audibly and/or visually alerts the medical personnel to the abnormal pressure condition on the patient's orbital area 110, and the patient's head is readjusted to correct this condition.

Some pressure on the site sensor 200 may be tolerable. Accordingly, in another embodiment of the monitor system 100 and method, the monitor 250 may actuate an alarm when the detected pressure is greater than a predetermined threshold or baseline, which is greater than zero pressure.

Pressure data from multiple patients at multiple sites is collected for a database as a research tool to determine normal pressure ranges for any eye (or other positional injury).

In the immediate following paragraphs, features that may be part of one or more implementations of the monitoring system 100 and/or the site sensors 200 described herein are indicated.

For example, in one or more implementations of the system 100, the system 100 may include one or more of the following. The entire system 100 is contained in a single unit. The site sensor 200 and the monitor 210 are integrated with each other. The site sensor 200 and the monitor 210 are connected to each other with any mechanical connection device. The site sensor 200 and the monitor 210 are connected to each other with any electrical connection device. The site sensor 200 and the monitor 210 are wirelessly connected to each other with any wireless equipment. The site sensor 200 and the monitor 210 are connected to each other with any hollow fiber or solid fiber device. The site sensor 200 and the monitor 210 are connected via any telemetering type equipment. The site sensor 200 and the monitor 210 are connected via any optical/photonic type equipment. The site sensor 200 and the monitor 210 are connected via any combination of equipment type. The site sensor 200 and the monitor 210 are connected with a conductive wire, set of wires, coiled wire set or any other form of conductive wiring or cable as know to those skilled in the art.

In one or more implementations of the site sensor 200, the site sensors 200 may include one or more of the following. The facial cushion support 300 is or includes the site sensor(s) 200. The pair of site sensors 200 may be a single site sensor or the pair of sites sensors 200 may be integrated into a single sensor device. The site sensor 200 may include a test section to allow for functional verification of the site sensor 200. The site sensor 200 senses external touch, pressure, and/or motion. The site sensor 200 is one or more of an electrochemical transducer, an electromechanical transducer, an electroacoustic transducer, a photoelectric transducer, an electromagnetic transducer, a magnetic transducer, an electrostatic transducer, a thermoelectric transducer, an electronic transducer, an electrical transducer, and a mechical transducer. The site sensor 200 is disposable. The site sensor 200 is reusable. The site sensor 200 has a limited life cycle or number of uses. The site sensor 200 is active. The site sensor 200 is reactive to one or more of contact, stress, movement, acceleration, temperature, light, mechanical, chemical, electrical or electronic property, and any other measurable physical property. The site sensor 200 reacts in the absence of any one of contact, stress, temperature, movement, acceleration, light, electrical or electronic property, mechanical, chemical, optical or any other physical property of the site sensor 200 being monitored. The active sensing area of the site sensor 200 is made of wire, traces, various conductive material, metals, painted traces, liquid conductive applications, sputtered deposition, vapor deposition build up, MEMs production, photolithography, or other electrical connection production method. The site sensor 200 is in any shape, configuration, construction, thickness, or curvature as may be desirable for application to orbital area or differing areas of the body. The site sensor 200 is two-dimensional, three-dimensional, polygonal, rectilinear, and/or curvilinear. The site sensor 200 contents and construction may be monolithic or of discrete components. One or more members of the site sensor 200 are sewn, bonded, connectored, sealed, fused, adhesively attached, glued, melted together or connected by any other method known to those skilled in the art. The site sensor 200 monitors any physical property that can be measured or gauged.

In one or more implementations of the site sensor 200, the input to the site sensor 200 may include one or more of the following. The input to the site sensor 200 is a direct current (DC) voltage potential. The input to the site sensor 200 is an alternating current (AC) voltage potential. The input to the site sensor 200 is an amplitude modulated (AM) signal. The input to the site sensor 200 is a frequency modulated (FM) signal. The input to the site sensor 200 is a pulse width modulated signal. The input to the site sensor 200 is a light source (of any wavelength). The input to the site sensor 200 is part of the electromagnetic spectrum. The input to the site sensor 200 is a thermal change. The input to the site sensor 200 is a mechanical force. The input to the site sensor 200 is an electrochemical change. The input to the site sensor 200 is any combination of inputs. The sensor input is sent to a computer file. The sensor input is sent to an electronic storage or media device. The sensor input is displayed on a computer monitor. The sensor input is displayed on a medical device's user interface. The input to the site sensor 200 is different from the output. The site sensor 200 operates in multiple or singular modalities. The site sensor 200 operation may change modalities.

In one or more implementations of the site sensor 200, the output from the site sensor 200 may include one or more of the following. The output from the site sensor 200 is electrical, mechanical, chemical, thermal, optical, or any other type of output. The output from the site sensor 200 is a direct current (VDC) voltage potential. The output from the site sensor 200 is an alternating current (VAC) voltage potential. The output from the site sensor 200 is an amplitude modulated (AM) signal. The output from the site sensor 200 is a frequency modulated (FM) signal. The output from the site sensor 200 is a pulse width modulated signal. The output from the site sensor 200 is a light source (of any wavelength). The output from the site sensor 200 is part of the electromagnetic spectrum. The output from the site sensor 200 is a mechanical force. The output from the site sensor 200 is an electrochemical change. The output from the site sensor 200 is any combination of outputs. The site sensor 200 output is different from the input. The sensor input is different from the output. The sensor output is sent to a computer file. The sensor output is sent to an electronic data storage or media device. The sensor output is displayed on a computer monitor. The sensor output is displayed on a medical device's user interface. The sensor output is variable.

The system 100 and method monitor external pressure on the orbital areas 110 of a patient 120 during prone position spinal surgery to detect a pressure condition on the orbital areas 110. If a pressure condition on the orbital areas 110 occurs, the monitor 210 detects this condition, and indicates an alarm (audible and/or visual). The patient's head is readjusted to correct this condition, and prevent eye-related positional injuries.

With reference to FIGS. 5-7, an alternative embodiment of a site sensor 400 will be described. The site sensor 400 may be used to monitor excessive external pressure incurred by a patient in any location on the patient's body (where the patient is placed in any position during any surgical procedure). The site sensor 400 is a substantially circular transducer patch and is made up of one or more appropriate medical-grade, biocompatible materials. The site sensor 400 includes a substantially flat transducer element 430 and a substantially annular ring 440 extending circumferentially outward from the periphery of the transducer element 430. An underside 450 of the ring 440 may be completely or partially coated or circumscribed with a coating of medical-grade, biocompatible adhesive, which is covered by a removable backing, to allow for the attachment of the site sensor 400 to the overlying dermis of a suspected external positional induced pressure point. Similar to the site sensor 200, one or more lead wires may extend from the transducer element 430 and be connected to a monitor for monitoring the condition of the site sensor 400. Use of the site sensor 400 is similar to that described above with respect to site sensor(s) 200. Thus, the site sensors and methods described herein may be used to monitor all external pressure capable of producing nerve damage, tissue damage, and/or any other physiological damage resulting from a positional injury during any surgical procedure where the patient is anesthetized, regardless of the patient's body position during the surgical procedure.

It will be readily apparent to those skilled in the art that still further changes and modifications in the actual concepts described herein can readily be made without departing from the spirit and scope of the invention as defined by the following claims.

What is claimed is:

1. A method of preventing eye-related positional injuries during spinal surgery, comprising:
   putting a spinal surgery patient under general anesthesia;
   adding an ointment to the surface of the eyeballs of the patient;
   maintaining the patient's eyelids in a closed condition during the spinal surgery;
   providing at least one site sensor to detect pressure on orbital areas of the patient, the at least one site sensor including a transducer in the form of a cupped, convex transducer element and a substantially annular ring extending circumferentially outward from the transducer element;
   adhering the ring of the at least one site sensor to the patient over the orbital areas of the patient so that the cupped, convex transducer element forms a protective convex barrier in front of the orbital areas and does not contact the eyeballs or eyelids;
   providing a facial support to support the patient's face during the spinal surgery, the facial support including an opening to accommodate the at least one site sensor on the orbital areas of the patient;
   providing the patient in a prone position with the patient's face supported by the facial support with the at least one site sensor accommodated by the opening;

connecting the at least one site sensor to a monitor to monitor pressure on the orbital areas of the patient with the at least one site sensor;

continuously monitoring pressure on the protective convex barrier formed by the cupped, convex transducer element in front of the orbital areas of the patient with the at least one site sensor and the monitor;

alerting medical personnel of a pressure condition on the protective convex barrier formed by the cupped, convex transducer element in front of the orbital areas if the monitor and the at least one site sensor determines a pressure condition exists on the protective convex barrier formed by the cupped, convex transducer element in front of the orbital areas;

readjusting the patient's head to alleviate the pressure condition, thereby preventing eye-related positional injuries.

2. The method of claim 1, wherein the at least one site sensor includes a pair of site sensors, one for each eye of the patient, and the method further includes adhering the pair of site sensors to the patient over the orbital areas of each eye of the patient.

3. The method of claim 1, further including the transducer causing a change in signal to the monitor upon a pressure condition, and the monitor detecting the change in signal and causing an alarm to be actuated to alert medical personnel of a pressure condition.

4. The method of claim 1, further including the monitor causing an alarm to be actuated to alert medical personnel of a pressure condition when detected pressure is greater than a predetermined threshold.

5. The method of claim 1, wherein the at least one site sensor includes one or more wires to connect the at least one site sensor to the monitor, and connecting includes connecting the at least one site sensor to the monitor with the one or more wires.

6. A method of preventing eye-related positional injuries during spinal surgery, comprising:

attaching at least one site sensor to a spinal surgery patient over orbital areas of the patient, the at least one site sensor including a transducer in the form of a cupped, convex transducer element and a substantially annular ring extending circumferentially outward from the transducer element, the substantially annular ring adhered to the patient over the orbital areas of the patient so that the cupped, convex transducer element forms a protective convex barrier in front of the orbital areas and does not contact the eyeballs or eyelids;

connecting the at least one site sensor to a monitor;

continuously monitoring pressure on the protective convex barrier formed by the cupped, convex transducer element in front of the orbital areas of the patient with the at least one site sensor and the monitor;

alerting medical personnel of a pressure condition on the protective convex barrier formed by the cupped, convex transducer element in front of the orbital areas if the monitor and the at least one site sensor determine a pressure condition exists on the protective convex barrier formed by the cupped, convex transducer element in front of the orbital areas;

readjusting the patient's head to alleviate the pressure condition, thereby preventing eye-related positional injuries.

7. The method of claim 6, wherein the at least one site sensor includes a pair of site sensors, one for each eye of the patient, and the method further includes adhering the pair of site sensors to the patient over the orbital areas of each eye of the patient.

8. The method of claim 6, further including the transducer causing a change in signal to the monitor upon a pressure condition, and the monitor detecting the change in signal and causing an alarm to be actuated to alert medical personnel of a pressure condition.

9. The method of claim 6, further including the monitor causing an alarm to be actuated to alert medical personnel of a pressure condition when detected pressure is greater than a predetermined threshold.

10. The method of claim 6, wherein the at least one site sensor includes one or more wires to connect the at least one site sensor to the monitor, and connecting includes connecting the at least one site sensor to the monitor with the one or more wires.

11. A method of preventing eye-related positional injuries during spinal surgery, comprising:

providing an orbital area pressure monitoring system including at least one site sensor with a transducer in the form of a cupped, convex transducer element and a substantially annular ring extending circumferentially outward from the transducer element, and a monitor connected to the at least one site sensor;

adhering the ring of the at least one site sensor to the patient over orbital areas of the patient so that the cupped, convex transducer element forms a protective convex barrier in front of the orbital areas and does not contact the eyeballs or eyelids;

using the orbital area pressure monitoring system to continuously monitor pressure on the protective convex barrier formed by the cupped, convex transducer element in front of the orbital areas of the patient with the at least one site sensor and monitor; and causing an alarm to be actuated to alert medical personnel of a pressure condition when monitored pressure is greater than a predetermined threshold.

12. The method of claim 11, wherein the at least one site sensor includes a pair of site sensors, one for each eye of the patient, and the method further includes adhering the pair of site sensors to the patient over the orbital areas of each eye of the patient.

13. The method of claim 11, further including the transducer causing a change in signal to the monitor upon a pressure condition, and the monitor detecting the change in signal and causing an alarm to be actuated to alert medical personnel of a pressure condition.

14. The method of claim 11, wherein the at least one site sensor includes one or more wires to connect the at least one site sensor to the monitor, and further including connecting the at least one site sensor to the monitor with the one or more wires.

* * * * *